(12) United States Patent
Jang

(10) Patent No.: US 12,042,350 B2
(45) Date of Patent: Jul. 23, 2024

(54) FACIAL MODEL FOR GENERATION OF POST-TREATMENT IMAGES OF TEETH AND SOFT FACIAL TISSUES

(71) Applicant: Align Technology, Inc., San Jose, CA (US)

(72) Inventor: Andrew Jang, San Mateo, CA (US)

(73) Assignee: Align Technology, Inc., San Jose, CA (US)

( * ) Notice: Subject to any disclaimer, the term of this patent is extended or adjusted under 35 U.S.C. 154(b) by 483 days.

(21) Appl. No.: 17/234,214

(22) Filed: Apr. 19, 2021

(65) Prior Publication Data

US 2021/0236241 A1 Aug. 5, 2021

Related U.S. Application Data

(62) Division of application No. 16/102,528, filed on Aug. 13, 2018, now Pat. No. 10,980,612.

(51) Int. Cl.
*A61C 7/00* (2006.01)
*A61B 5/00* (2006.01)
(Continued)

(52) U.S. Cl.
CPC ............ *A61C 7/002* (2013.01); *A61B 5/4542* (2013.01); *A61B 34/10* (2016.02); *G06V 40/168* (2022.01);
(Continued)

(58) Field of Classification Search
CPC . A61C 7/002; A61C 2007/004; A61B 5/4542; A61B 34/10; A61B 90/36; A61B 2017/00216; A61B 2034/105; A61B 2034/2065; A61B 5/743; A61B 90/361; A61B 2034/104; A61B 2090/364; A61B 2090/372; G06V 40/168; G06V 40/174; G06V 20/20; G06V 40/171; G06F 3/011; G06T 2219/2021; G06T 19/20; G16H 40/67; G16H 50/50
See application file for complete search history.

(56) References Cited

U.S. PATENT DOCUMENTS 7,001,270 B2   2/2006   Taub
7,383,198 B1   6/2008   Sepe
(Continued)

*Primary Examiner* — Santiago Garcia
(74) *Attorney, Agent, or Firm* — LOWENSTEIN SANDLER LLP

(57) ABSTRACT

A processing device receives a pre-treatment model of upper and lower dental arches of a person, the pre-treatment model comprising first positions of teeth, and further receives a post-treatment model of the upper and lower dental arches, the post-treatment model comprising second positions of the teeth. The processing device determines a first mapping between first positions of first landmarks in the pre-treatment model and second positions of the first landmarks in the post-treatment model, and receives an image of a face of the person, comprising at least the teeth and soft facial tissues. The processing device generates a second mapping between the first landmarks and second landmarks associated with the soft facial tissues from the image, and generates a facial model comprising the first mapping and the second mapping, wherein the facial model generates post-treatment images of the teeth and the soft facial tissues based on pre-treatment images.

24 Claims, 6 Drawing Sheets

(51) Int. Cl.
*A61B 17/00* (2006.01)
*A61B 34/10* (2016.01)
*A61B 34/20* (2016.01)
*A61B 90/00* (2016.01)
*G06F 3/01* (2006.01)
*G06V 40/16* (2022.01)

(52) U.S. Cl.
CPC .. *G06V 40/174* (2022.01); *A61B 2017/00216* (2013.01); *A61B 2034/105* (2016.02); *A61B 2034/2065* (2016.02); *A61B 90/36* (2016.02); *G06F 3/011* (2013.01)

(56) References Cited

U.S. PATENT DOCUMENTS

| | | | |
|---|---|---|---|
| 7,580,846 B2 | 8/2009 | Chishti et al. | |
| 7,870,280 B2 | 1/2011 | Kuo | |
| 7,904,307 B2 | 3/2011 | Abolfathi et al. | |
| 7,987,099 B2 | 7/2011 | Kuo et al. | |
| 8,024,198 B2 | 9/2011 | Kuo | |
| 8,706,672 B2 * | 4/2014 | Malfliet | G06F 17/00 264/16 |
| 8,738,394 B2 | 5/2014 | Kuo | |
| 9,907,626 B1 * | 3/2018 | Lowe | A61C 7/008 |
| 10,467,815 B2 | 11/2019 | Marom et al. | |
| 10,504,386 B2 | 12/2019 | Levin et al. | |
| 10,595,966 B2 | 3/2020 | Carrier, Jr. et al. | |
| 10,695,150 B2 | 6/2020 | Kopelman et al. | |
| 10,885,521 B2 | 1/2021 | Miller et al. | |
| 10,888,399 B2 | 1/2021 | Kopelman et al. | |
| 10,980,612 B2 | 4/2021 | Jang | |
| 10,980,613 B2 | 4/2021 | Shanjani et al. | |
| 2002/0188478 A1 | 12/2002 | Breeland et al. | |
| 2005/0159986 A1 | 7/2005 | Breeland et al. | |
| 2006/0154198 A1 * | 7/2006 | Durbin | G06T 17/00 433/29 |
| 2008/0288289 A1 | 11/2008 | Sah | |
| 2010/0191510 A1 * | 7/2010 | Kopelman | A61C 19/045 703/1 |
| 2012/0015316 A1 * | 1/2012 | Sachdeva | G16H 40/20 382/128 |
| 2013/0218531 A1 * | 8/2013 | Deichmann | A61C 5/77 703/1 |
| 2015/0079533 A1 * | 3/2015 | Lowe | G16H 20/40 433/24 |
| 2015/0265374 A1 * | 9/2015 | Masoud | G06V 40/171 382/128 |
| 2016/0361140 A1 * | 12/2016 | Lowe | A61C 7/002 |
| 2020/0008877 A1 * | 1/2020 | Jo | A61C 1/084 |
| 2020/0160947 A1 | 5/2020 | Rasovsky et al. | |
| 2020/0268495 A1 * | 8/2020 | Ryakhovsky | A61C 19/05 |

\* cited by examiner

200

```
┌─────────────────────────────────────────────────────────────────────────────┐
│ Receive a pre-treatment virtual 3D model of an upper dental arch and a      │
│ lower dental arch of a person, the pre-treatment virtual 3D model           │
│ comprising first positions and orientations of teeth of the upper dental    │
│ arch and the lower dental arch 210                                          │
└─────────────────────────────────────────────────────────────────────────────┘
                                      ▼
┌─────────────────────────────────────────────────────────────────────────────┐
│ Receive a post-treatment virtual 3D model of the upper dental arch and the  │
│ lower dental arch of the person, the post-treatment virtual 3D model        │
│ comprising second positions and orientations of the teeth of the upper      │
│ dental arch and the lower dental arch, wherein for at least one tooth the   │
│ second positions and orientations are different from the first positions    │
│ and orientations 215                                                        │
└─────────────────────────────────────────────────────────────────────────────┘
                                      ▼
┌─────────────────────────────────────────────────────────────────────────────┐
│ Determine a first mapping between first positions of a first plurality of   │
│ visual landmarks associated with the teeth in the pre-treatment virtual 3D  │
│ model and second positions of the first plurality of visible landmarks      │
│ associated with the teeth in the post-treatment virtual 3D model 220        │
└─────────────────────────────────────────────────────────────────────────────┘
                                      ▼
┌─────────────────────────────────────────────────────────────────────────────┐
│ Receive an image of a face of the person, wherein the image comprises at    │
│ least a portion of the teeth and soft facial tissues 225                    │
└─────────────────────────────────────────────────────────────────────────────┘
                                      ▼
┌─────────────────────────────────────────────────────────────────────────────┐
│ Generate a second mapping between the first plurality of visual landmarks   │
│ associated with the teeth and a second plurality of visual landmarks        │
│ associated with the soft facial tissues from the image of the face of the   │
│ person 230                                                                  │
└─────────────────────────────────────────────────────────────────────────────┘
                                      ▼
┌─────────────────────────────────────────────────────────────────────────────┐
│ Generate a facial model comprising the first mapping and the second         │
│ mapping, wherein the facial model generates post-treatment images of the    │
│ teeth and the soft facial tissues based on pre-treatment images of the      │
│ teeth and the soft facial tissues 240                                       │
└─────────────────────────────────────────────────────────────────────────────┘
```

FIG. 2

FACIAL MODEL FOR GENERATION OF POST-TREATMENT IMAGES OF TEETH AND SOFT FACIAL TISSUES

RELATED APPLICATIONS

The present application is a divisional application of U.S. patent application Ser. No. 16/102,528, filed Aug. 13, 2018, which is incorporated by reference herein.

TECHNICAL FIELD

Embodiments of the present disclosure relate to the field of dentistry and, in particular, to a system and method for generating an image of a face showing a post treatment dentition and soft tissues, where the image responds to facial expressions of a person in the field of view of an image sensor.

BACKGROUND

It is often useful for a dental practitioner to be able to show a patient or prospective patient what that patient's face will look like after orthodontic treatment or other dental treatment. The standard technique to show the patient what their post-treatment smile will look like is called smile design. For smile design, the dental practitioner makes a physical mold of the patient's mouth, waxes the physical mold, places putty over the mold, and contours the putty to show what the patient's teeth might look like post treatment. The mold is then placed in the patient's mouth, and the patient can examine their face in a mirror, moving their face through different facial expressions to see how their face looks in each of the facial expressions.

The smile design process is a manual process that is time consuming. Additionally, since a physical mold is made and then placed over the patient's existing dentition, the smile design process is limited to showing the teeth with added material (e.g., added material to show increased lip support). However, if the patient has a malocclusion that causes the patient's lip to jut out, there is no way to show the patient's post-treatment smile or facial expressions via the smile design technique.

BRIEF DESCRIPTION OF THE DRAWINGS

Embodiments of the present disclosure are illustrated by way of example, and not by way of limitation, in the figures of the accompanying drawings.

FIG. 2 illustrates a flow diagram for a method of generating a facial model for simulating post-treatment images of faces based on pre-treatment images of those faces, in accordance with an embodiment.

DETAILED DESCRIPTION

Figure 1:
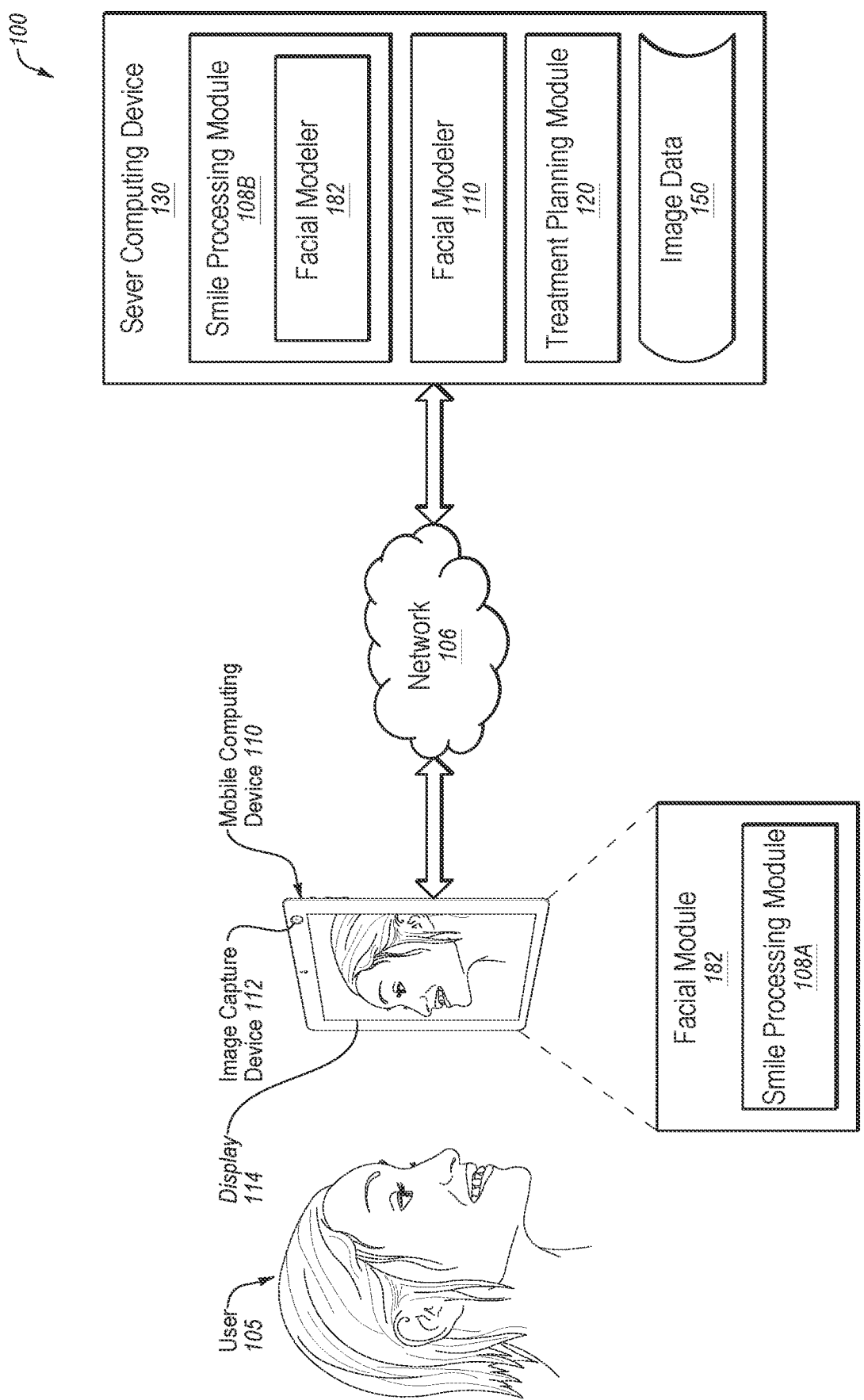
FIG. 1 illustrates one embodiment of a system for generating and outputting simulated post-treatment images of faces, in accordance with an embodiment.

Described herein are methods and apparatuses for generating images of smiles that show post-treatment dentition and post-treatment soft tissues of a person's face.

In embodiments, a computing device (e.g., a server computing device) receives a pre-treatment virtual three-dimensional (3D) model of an upper dental arch and a lower dental arch of a person, the pre-treatment virtual 3D model comprising first positions and orientations of teeth of the upper dental arch and the lower dental arch. The computing device also receives a post-treatment virtual 3D model of the upper dental arch and the lower dental arch of the person, the post-treatment virtual 3D model comprising second positions and orientations of the teeth of the upper dental arch and the lower dental arch, wherein for at least one tooth the second positions and orientations are different from the first positions and orientations. The computing device may determine a first mapping between first positions of a first plurality of landmarks (e.g., visible or visual landmarks) associated with the teeth in the pre-treatment virtual 3D model and second positions of the first plurality of landmarks associated with the teeth in the post-treatment virtual 3D model. The pre-treatment virtual 3D model, the post-treatment virtual 3D model and/or the first mapping may be included in a treatment plan that may be received by the computing device. The computing device receives an image of a face of the person, wherein the image comprises at least a portion of the teeth and soft facial tissues. The image may be a cone beam computed tomography (CBCT) image, one or more x-ray images, a panoramic x-ray image, a 3D optical image and/or other imaging modality. The image shows both soft tissues and bony structures (e.g., teeth, jaw bone, etc.) of the person's face. The computing device generates a second mapping between the first plurality of landmarks associated with the teeth and a second plurality of landmarks (e.g., visible or visual landmarks) associated with the soft facial tissues from the image of the face of the person. The computing device may then generate a facial model comprising the first mapping and the second mapping. The facial model may be used to generate post-treatment images of the teeth and the soft facial tissues based on pre-treatment images of the teeth and the soft facial tissues.

The computing device may send the facial model to one or more additional computing devices that may have fewer processing resources than the computing device that generates the facial model. For example, the facial model may be sent to a mobile device (e.g., a mobile phone) of the person.

In further embodiments, a computing device receives a 3D image of a face of a person. The computing device may be, for example a mobile computing device such as a mobile phone or a tablet computer. The computing device identifies a first plurality of landmarks and a second plurality of landmarks on the face from the 3D image. The first plurality of landmarks may be associated with bony structures (e.g., teeth, jaw bone, cheek bone, etc.) and the second plurality of landmarks may be associated with soft facial tissues (e.g., cheeks, gums, lips, etc.). The computing device determines a post-treatment arrangement of the first plurality of landmarks based on a first mapping between a current dentition of the person and a post-treatment dentition of the person. The computing device further determines, based on applying the post-treatment arrangement of the first plurality of landmarks to a second mapping between the first plurality of landmarks and the second plurality of landmarks, a post-treatment shape of the soft facial tissues. The first mapping and the second mapping may be components of a facial model stored on the computing device in embodiments. The computing device generates a modified version of the 3D image, wherein the soft facial tissues have the post-treatment shape in the modified version of the 3D image.

The computing device may receive a stream of 3D images, and may generate modified versions of each image in the stream of 3D images. Accordingly, as a user moves their head, changes their facial expressions, etc., the computing device generates updated modified 3D images that reflect the current facial expressions, head positions, and so on. If the computing device includes an image sensor to generate the stream of 3D images and a display device to display the modified versions of the stream of 3D images, then the computing device can act as a virtual mirror that shows the person their post-treatment face in real time, including their teeth, facial contours (e.g., lip support, changes to smile line, etc.), soft tissues, and so on.

The simulated post-treatment images generated in embodiments are able to show post-treatment smiles with modified dentition as well as modified soft tissues. This enables the post-treatment images to be photo-realistic and close to what their smiles would actually look like after dental treatment. Post-treatment images may depict changes that cannot be shown by the traditional physical smile design process.

FIG. 1 illustrates one embodiment of a system 100 that generates post-treatment images of smiles based on pre-treatment images of the smiles. In one embodiment, the system 100 includes a mobile computing device 110 connected to a server computing device 130 via a network 108. Mobile computing device 110 may be, for example, a mobile phone (e.g., such as an iPhone®, an Android® phone, etc.), a tablet computing device, a notebook computer, a laptop computer, a digital camera, a portable game console, and so on. Alternatively, a traditionally stationary computing device may be used instead of the mobile computing device 110. Examples of traditionally stationary computing devices include desktop computers, server computers (e.g., rackmount server computers), game consoles, set top boxes, and so on. In some embodiments, the mobile computing device 110 may instead be, for example, a smart television.

Server computing device 130 may include physical machines and/or virtual machines hosted by physical machines. The physical machines may be rackmount servers, desktop computers, or other computing devices. The physical machines may include a processing device, memory, secondary storage, one or more input devices (e.g., such as a keyboard, mouse, tablet, speakers, or the like), one or more output devices (e.g., a display, a printer, etc.), and/or other hardware components. In one embodiment, the server computing device 130 includes one or more virtual machines, which may be managed and provided by a cloud provider system. Each virtual machine offered by a cloud service provider may be hosted on one or more physical machine. Server computing device 130 may be connected to data store either directly or via a network.

The network 108 may be a local area network (LAN), a public wide area network (WAN) (e.g., the Internet), a private WAN (e.g., an intranet), or a combination thereof.

Server computing device 130 may include a smile processing module 108B, a facial modeler 112 and/or a treatment planning module 120 in embodiments. The treatment planning module 120 is responsible for generating a treatment plan 155 that includes a treatment outcome for a patient, such as user 105. The treatment plan 155 may include and/or be based on image data 150, which may include an initial 2D and/or 3D image of the patient's dental arches. For example, the image data 150 may include 3D intraoral images of the patient's dental arches, and the treatment planning module 120 may stitch the 3D images together to create a virtual 3D model of the dental arches. Alternatively, the 2D or 3D images may be of a physical mold (e.g., an impression) of the patient's dental arches. The treatment planning module 120 may then determine current positions and orientations of the patient's teeth from the virtual 3D model and determine target final positions and orientations for the patient's teeth represented as a treatment outcome. The treatment planning module 120 may then generate a virtual 3D model showing the patient's dental arches at the end of treatment as well as one or more virtual 3D models showing the patient's dental arches at various intermediate stages of treatment. These various virtual 3D models may be included in the treatment plan 155.

By way of non-limiting example, a treatment outcome may be the result of a variety of dental procedures. Such dental procedures may be broadly divided into prosthodontic (restorative) and orthodontic procedures, and then further subdivided into specific forms of these procedures. Additionally, dental procedures may include identification and treatment of gum disease, sleep apnea, and intraoral conditions. The term prosthodontic procedure refers, inter alia, to any procedure involving the oral cavity and directed to the design, manufacture or installation of a dental prosthesis at a dental site within the oral cavity, or a real or virtual model thereof, or directed to the design and preparation of the dental site to receive such a prosthesis. A prosthesis may include any restoration such as implants, crowns, veneers, inlays, onlays, and bridges, for example, and any other artificial partial or complete denture. The term orthodontic procedure refers, inter alia, to any procedure involving the oral cavity and directed to the design, manufacture or installation of orthodontic elements at a dental site within the oral cavity, or a real or virtual model thereof, or directed to the design and preparation of the dental site to receive such orthodontic elements. These elements may be appliances including but not limited to brackets and wires, retainers, clear aligners, or functional appliances. Any of treatment outcomes or updates to treatment outcomes described herein may be based on these orthodontic and/or dental procedures. Examples of orthodontic treatments are treatments that reposition the teeth, treatments such as mandibular advancement that manipulate the lower jaw, treatments such as palatal expansion that widen the upper and/or lower palate, and so on. For example, an update to a treatment outcome may be generated by interaction with a user to perform one or more procedures to one or more portions of a patient's dental arch or mouth. Planning these orthodontic procedures and/or dental procedures may be facilitated by the AR system described herein.

A treatment plan 155 for producing a particular treatment outcome may be generated by first performing an intraoral scan of a patient's oral cavity to generate image data comprising multiple 3D images of the patient's upper and lower dental arches. Alternatively, a physical mold may be taken of the patient's upper and lower dental arches, and a scan may be performed of the mold. From the intraoral scan (or scan of the mold) a virtual 3D model of the upper and/or lower dental arches of the patient may be generated. A dental practitioner may then determine a desired final position and orientation for the patient's teeth on the upper and lower dental arches, for the patient's bite, and so on. This information may be used to generate the virtual 3D model of the patient's upper and/or lower arches after orthodontic treatment. This data may be used to create the orthodontic treatment plan 155. The orthodontic treatment plan 155 may include a sequence of orthodontic treatment stages. Each orthodontic treatment stage may adjust the patient's dentition by a prescribed amount, and may be associated with a 3D model of the patient's dental arch that shows the patient's dentition at that treatment stage.

In some embodiments, the treatment planning module 120 may receive or generate one or more virtual 3D models, virtual 2D models, or other treatment outcome models based on received intraoral images. For example, an intraoral scan of the patient's oral cavity may be performed to generate an initial virtual 3D model of the upper and/or lower dental arches of the patient. Treatment planning module 120 may then determine a final treatment outcome based on the initial virtual 3D model, and then generate a new virtual 3D model representing the final treatment outcome.

Server computing device 130 may receive a treatment plan 155 and/or image data 150 for a user 105. In some embodiments, the image data 150 is included in the treatment plan 155. The image data 150 may include the aforementioned intraoral images of the patient's upper and/or lower dental arches and/or may include one or more images that show both bony structures and soft tissues of the patient's face. Examples of bony structures include teeth, upper and lower jaw bones, cheek bones, skull, and so on. Examples of soft tissues include lips, gums, skin (e.g., subcutaneous layer, cutaneous layer, etc.), muscles, fat, ligaments, and so on. The soft tissues may show, for example, lip protrusion, facial contours, smile line, and so on. The image data 150 showing the bony structures and the soft tissues may be or include 3D image data and/or 2D image data.

In one embodiment, the image data 150 includes one or more x-ray images. For example, the image data 150 may include CBCT image data. During dental/orthodontic imaging using a CBCT scanner, the CBCT scanner rotates around the patient's head, obtaining a set of distinct images (e.g., up to nearly 600 distinct images). Scanning software collects the data and reconstructs it, producing 3D digital volume composed of three-dimensional voxels of anatomical data that includes both bony structures and soft tissues. Alternatively, the image data 150 may include traditional dental x-rays from one or more views, x-ray data from a computed tomographic (CT) scan, a panoramic x-ray image, a cephalogram, and so on.

In embodiments, the image data 150 may be or include one or more optical images, which may include 3D optical images and/or 2D optical images. The optical images may show bony structures such as teeth as well as soft tissues. The optical images may also show fixed locations that do not move with changes in facial expression, such as eyes, nose, and so on.

Facial modeler 110 uses the image data 150 and the treatment plan 155 to generate a facial model 182 for the patient (e.g., user 105). A pre-treatment virtual 3D model of the upper and lower dental arches of the patient as well as a post-treatment virtual 3D model of the upper and lower dental arches of the patient may be used by facial modeler 112 together with the image data 150 (e.g., a 3D digital volume produced from a CBCT scan) to produce the facial model 182. To generate the facial model 182, the facial modeler 112 may generate a first mapping between the current and final positions of visible landmarks associated with teeth of the patient. The visible landmarks may be landmarks that will show up in an optical image (e.g., such as points on one or more teeth of the patient). The first mapping may also be between current and final positions of one or more non-visible landmarks of bony structures that might not show up in optical images. Alternatively, such a first mapping may be included in the treatment plan 155 generated by treatment planning module 120.

Facial modeler 110 may additionally use the image data 150 to generate a second mapping between the first visible landmarks and second visible landmarks associated with soft tissues on the patient's face. For example, the second mapping may be between points on teeth and points on the cheeks and/or on the lips, and so on. The second mapping may additionally map non-visible landmarks of bony structures to non-visible landmarks of soft tissues (e.g., internal soft tissues such as muscles, internal skin layers, ligaments, and so on). The first mapping may be used to determine final positions of the first landmarks post-treatment. The second mapping may be used to determine final positions of the second landmarks post-treatment based on the final positions of the first landmarks.

Facial modeler 110 may generate a facial model 182 that includes the first mapping and the second mapping. The facial model 182 may additionally generate functions that affect the relationships between the first landmarks and the second landmarks for different facial expressions. Different functions may be generated for different sets of landmarks. The functions that affect the relationships between the first landmarks and the second landmarks may be generated based on image data for the user 105, based on historical data for other patients and/or based on pedagogical data (e.g., data describing how different facial tissues respond to jaw motion). In one embodiment, the functions are generic functions generated based on historical and/or pedagogical data.

In some embodiments, the facial model 182 includes additional information based on a cephalometric analysis of the patient. Facial modeler 112 may determine one or more cephalometric characteristics based on received image data 150 (e.g., based on a CBCT scan, a panoramic x-ray image, and/or a cephalogram of the patient). The cephalometric characteristics may include one or more distances or angles describing the position of features of the patient's face relative to each other. In some embodiments, the facial modeler 112 may estimate changes to the cephalometric characteristics based on a treatment outcome for the patient.

Once the facial model 182 is generated, it may be provided to one or more smile processing modules 108A-B. In one embodiment, server computing device 130 sends the facial model 182 to mobile computing device 110 (or other computing device). The smile processing modules 108A-B may then process pre-treatment images using the facial model 182 to generate post-treatment images of the patient.

In embodiments, the mobile computing device 110 (or other computing device) includes an image capture device 113 and a display 114. Display 114 may be a liquid crystal display (LCD), a light emitting diode (LED) display, an organic LED (OLED) display, or other type of display. Additionally, the mobile computing device (or other computing device) 110 may include a smile processing module 108A, which may be or include a hardware module, a software module and/or a firmware module.

Image capture device 113 may be a 3D image capture device or a 2D image capture device. The image capture device 113 may be or include a charge-coupled device (CCD) sensor and/or a complementary metal-oxide semiconductor (CMOS) sensor. The image capture device 113 may generate images or video (e.g., a stream of images). In some embodiments, image capture device 113 is a 3D image capture device. The 3D image capture device may generate depth data using techniques such as stereoscopic imaging (e.g., by including two or more image sensors having known fixed orientations to one another), dot projection (e.g., using infrared dots), grid projection (e.g., using a projected infrared grid), or other 3D image capture technique.

Image capture device 113 may generate an image or video of user 105 smiling. The generated image (or sequence of images) may show a current pre-treatment dentition and facial features of the user 105, which may include one or more malocclusions, lip protrusion, a narrow smile showing dark triangles at the corners of the mouth where the smile extends beyond the teeth, and so on. Smile processing module 108A may process the captured image (or images) using the facial model 182 to generate one or more post-treatment facial images of the user 105. These one or more post-treatment facial images may then be output to the display 114 to show the user 105 his or her post-treatment smile in real-time (or near real-time). The smile processing module 108A may generate and output simulated post-treatment smiles to display 114 fast enough that the user 105 experiences a mirror-like effect. As the user 105 changes his or her facial expression, an updated image may be generated showing that same facial expression but with post-treatment dentition and soft facial tissues.

In one embodiment, smile processing module 108A outputs instructions for the user 105 to adopt a series of different facial expressions. Image capture device 113 may capture images of each of these facial expressions. Such captured images of the different facial expressions may then be sent over the network 106 to server computing device 130. Facial modeler 112 may use these captured images of the facial expressions to update or refine one or more functions that model the interaction between bony structures and facial tissues with changing expressions. Alternatively, facial modeler 112 may use the one or more images to generate the functions if they have not already been generated (e.g., if facial model 182 has not yet been generated). In one embodiment, facial modeler 112 replaces weights and/or parameters of one or more functions to replace generic functions with user specific functions. Such user specific functions may model the actual mechanics of how different soft tissues of the user 105 respond to facial expressions and movements. Once the one or more functions are updated (or generated), facial modeler 112 may generate an updated or new facial model 182 that may include the first mapping, the second mapping and the one or more functions. Server computing device 130 may then transmit the new or updated facial model 182 to mobile computing device 110 (or other computing device). Smile processing module 108A may then use the updated or new facial model 182 to generate accurate photo-realistic post-treatment images of the user 105 based on pre-treatment images captured by image capture device 113.

FIGS. 2-5 below describe example embodiments associated with generating a facial model for a user and applying the facial model to generate simulated post-treatment images of the patient's face. The examples are described with reference to flow charts describing processes of generating or applying such facial models. In addition, the flow charts provide example processes that may be performed by system 100. However, the processes performed by the system 100 may include fewer or additional blocks than shown, and in some embodiments the processes in the flow charts may be performed in a different order than shown. The methods depicted in FIGS. 2-5 may be performed by a processing logic that may comprise hardware (e.g., circuitry, dedicated logic, programmable logic, microcode, etc.), software (e.g., instructions run on a processing device to perform hardware simulation), or a combination thereof. Various embodiments may be performed by system 100, mobile computing device 110, and/or server computing device 130.

FIG. 2 illustrates a flow diagram for a method 200 of generating a facial model for simulating post-treatment images of faces based on pre-treatment images of those faces, in accordance with an embodiment. At block 210 of method 200, processing logic receives a pre-treatment virtual 3D model of an upper dental arch and a lower dental arch of a person. The pre-treatment virtual 3D model may include first positions and orientations of teeth of the upper dental arch and the lower dental arc. At block 215, processing logic receives a post-treatment virtual 3D model of the upper dental arch and the lower dental arch of the person. The post-treatment virtual 3D model may include second positions and orientations of the teeth of the upper dental arch and the lower dental arch. For at least one tooth of the person, the second positions and orientations are different from the first positions and orientations.

In one embodiment, the pre-treatment virtual 3D model and the post-treatment virtual 3D model are included in a received treatment plan. For example, a treatment outcome may have already been determined based on performing an intraoral scan of the patient's oral cavity, generating an initial virtual 3D model of the patient's dental arches, and then generating a final virtual 3D model of the target dental arches for the patient as they will be after orthodontic treatment. In one embodiment, the treatment plan is retrieved from storage. In one embodiment, the treatment plan, including the virtual 3D models, is generated by processing logic. For example, processing logic may generate the pre-treatment virtual 3D model and then determine a treatment outcome therefrom. The treatment outcome may be, for example, an orthodontic treatment outcome that shows a person's teeth in a straightened and aligned arrangement.

At block 220, processing logic determines a first mapping between first positions of a first set of visible landmarks (and optionally non-visible landmarks) associated with the teeth in the pre-treatment virtual 3D model and second positions of the set of visible landmarks (and optionally non-visible landmarks) associated with the teeth in the post-treatment virtual 3D model. Alternatively, the first mapping may have been previously computed and may be included in a received treatment plan.

At block 225, processing logic receives an image of a face of the person. The received image may include at least a portion of the teeth of the person and soft facial tissues of the person. The received image may include a 3D or 2D image generated by an image capture device integrated into or attached to a computing device (e.g., such as image capture device 113 of FIG. 1). Alternatively, or additionally, the received image may include one or more of a CBCT scan, a CT scan, one or more traditional x-ray images, a cephalogram, a panoramic x-ray image, and so on. The received image may include a representation of one or more of the visible landmarks indicated in the first mapping.

At block 230, processing logic generates a second mapping between the first set of visible landmarks associated with the teeth (and optionally other bony structures and/or fixed structures that will be visible in optical images) and a second set of visible landmarks (and optionally non-visible landmarks) associated with the soft facial tissues. The second mapping may be used to determine where the second set of landmarks should be repositioned to in response to changes in position of the first set of landmarks. Ultimately, the second mapping may be used to model the relationship between bony structures (e.g., teeth and jaw bones) and soft facial tissues (e.g., lips, gums, smile line, facial contours, etc.).

At block 240, processing logic generates a facial model that includes the first mapping and the second mapping. The facial model may be used to generate post-treatment images of the teeth and the soft facial tissues based on pre-treatment images of the teeth and the soft facial tissues. The imaging modality of the pre-treatment images that are input into the facial model may be a different imaging modality than was received at block 225 and used to generate the facial model in embodiments.

In some embodiments, the facial model generated in method 200 includes one or more functions that control how the relationships between the first landmarks and the second landmarks change with changes in facial expression. Such functions may include generic functions generated based on a large pool of patient data and/or based on pedagogical information in some embodiments.

The facial model (e.g., functions included in the facial model) may also model how light reacts to soft facial tissues, and may adjust coloration and/or texture with changes in facial expressions and/or light sources. For example, light may respond differently depending on the angle of inclination and/or the shape of the soft facial tissues. In some embodiments, different facial models are generated based on different images (e.g., received at block 225), where each of the images has different lighting conditions. Alternatively, a single model may be generated, but that single model may include one or more functions that take into account different lighting conditions. The model may be trained based on receiving multiple images, where those multiple images include different facial expressions and/or different lighting conditions.

Figure 3:
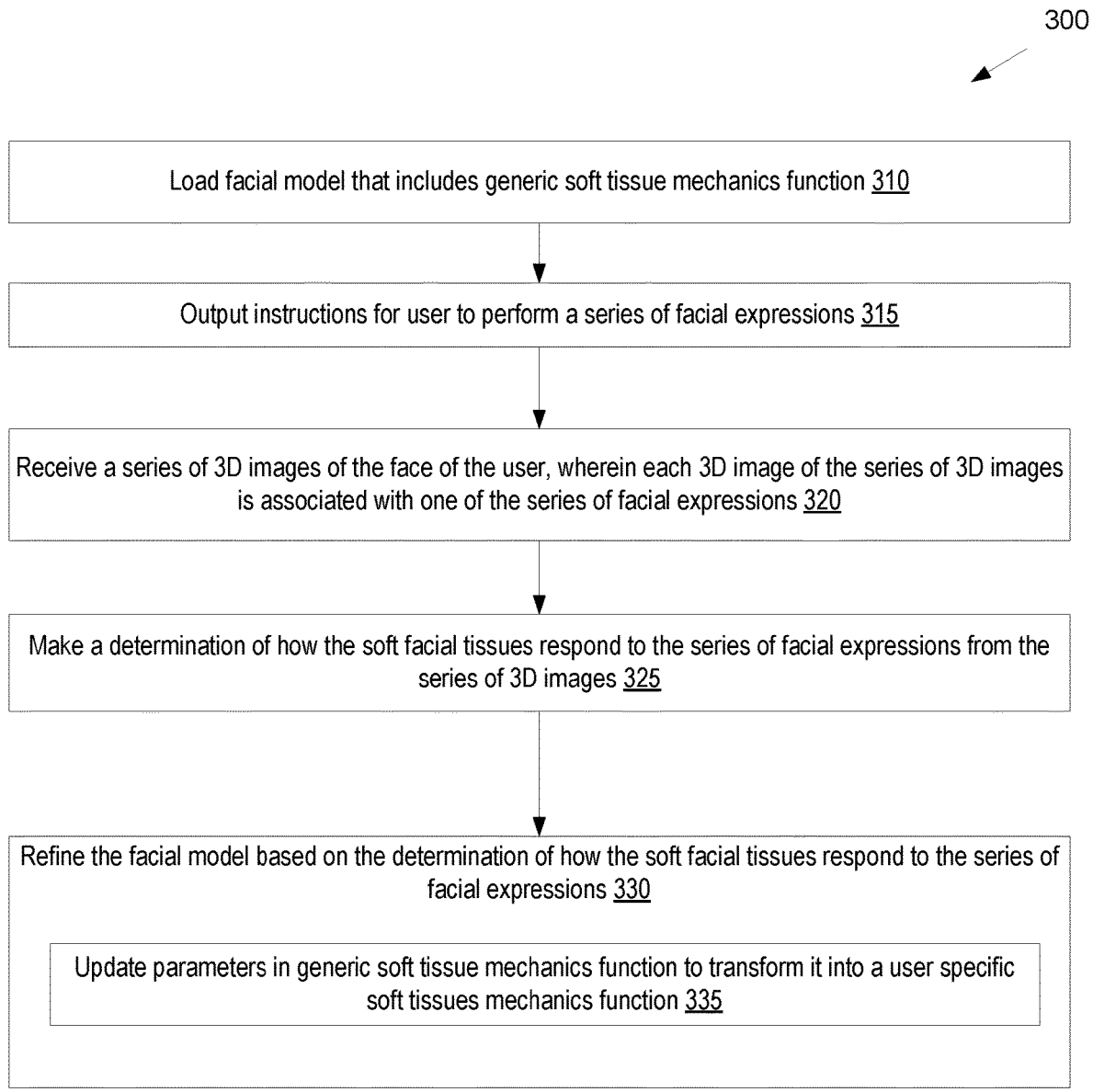
FIG. 3 illustrates a flow diagram for a method of refining a facial model, in accordance with an embodiment.

FIG. 3 illustrates a flow diagram for a method 300 of refining a facial model, in accordance with an embodiment. The facial model may have been generated as set forth in method 200 in embodiments. At block 310 of method 300, processing logic loads a facial model that includes a generic soft tissue mechanics function. The facial model may include multiple different generic soft tissue mechanics functions in embodiments. For example, the facial model may include different generic functions for the upper lip, the lower lip, the skin, the cheeks, the gums, ligaments, muscles, and so on. In one example, there are multiple different functions for the skin, where each function is associated with a different layer of skin.

At block 315, processing logic outputs instructions for a user to perform a series of facial expressions. At block 320, processing logic may receive a series of 3D images (or 2D images) of the face of a person or user. Each of the images in the series of images may be associated with one of the series of facial expressions. In each of the images, there may be a different relationship (e.g., different distance, different relative vertical position, different relative horizontal position, etc.) between a first set of landmarks and a second set of landmarks. These different relationships may be used at block 325 to make a determination of how the soft facial tissues respond to the series of facial expressions from the series of 3D images.

At block 330, processing logic refines the facial model based on the determination of how the soft facial tissues respond to the series of facial expressions. In one embodiment, this includes updating parameters or values in the generic soft tissue mechanics function or functions to transform these functions into one or more user specific soft tissue mechanics functions. For example, the weights associated with one or more terms of a soft tissue mechanics function may be computed or updated based on the determination made at block 325.

In one embodiment, a first computing device (e.g., mobile computing device 110) outputs the instructions at block 315 and generates the series of images. The first computing device may then send the images to a second computing device (e.g., server computing device 130), which may have loaded the facial model, receive the images from the first computing device, make the determination at block 325 and refine the facial model at block 330. The second device may then send the completed or updated facial model to the first computing device for later use.

Figure 4:
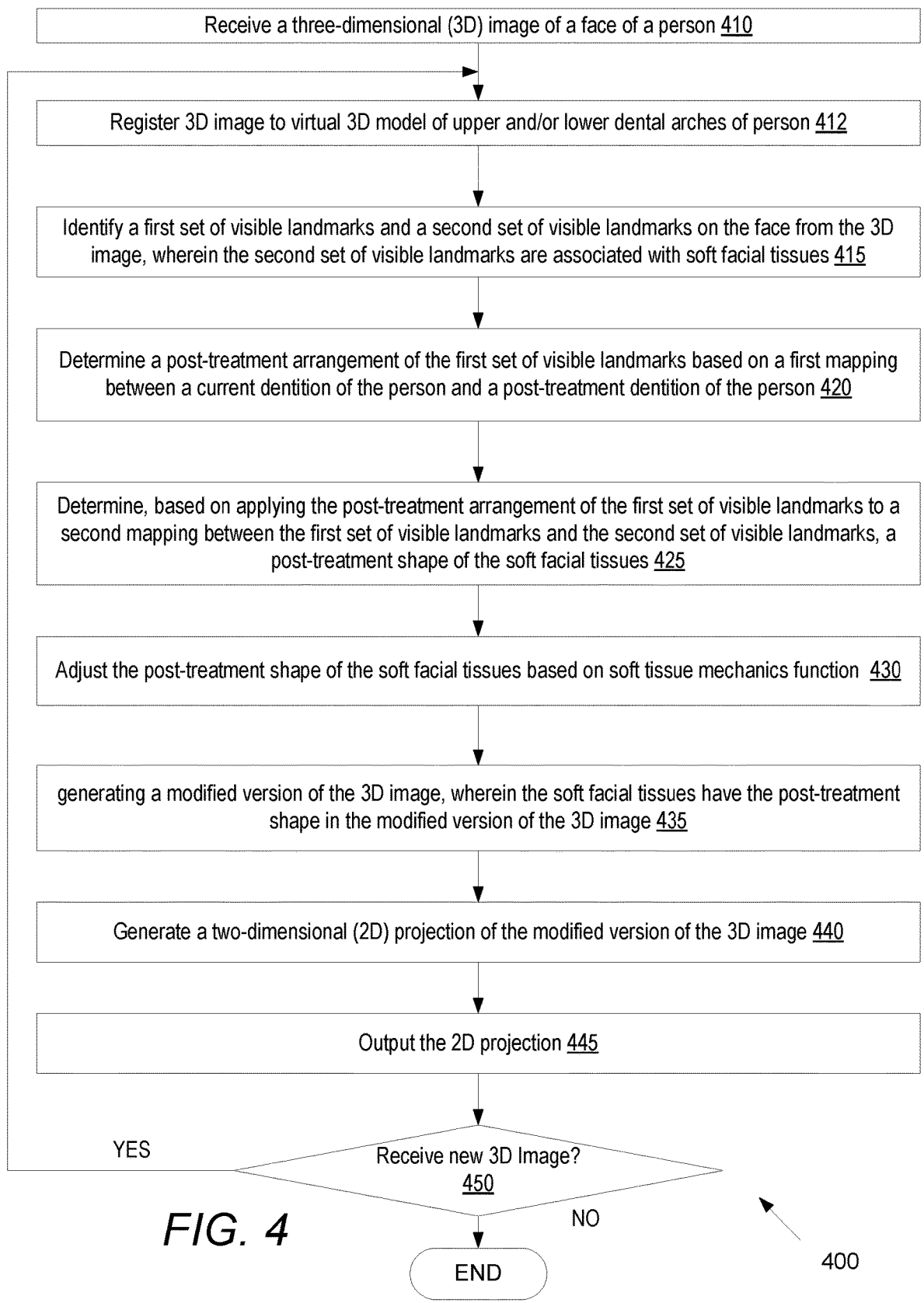
FIG. 4 illustrates a flow diagram for a method of simulating post-treatment images of faces based on pre-treatment images of those faces using a facial model, in accordance with an embodiment.

FIG. 4 illustrates a flow diagram for a method 400 of simulating post-treatment images of faces based on pre-treatment images of those faces using a facial model, in accordance with an embodiment. At block 410 of method 400, processing logic receives a 3D image of a face of a person. For example, processing logic of a mobile computing device may receive the 3D image. At block 412, processing logic registers the 3D image to a virtual 3D model of an upper and/or lower dental arch of the person. In one embodiment, processing logic sends the 3D image to a remote computing device (e.g., a server computing device) for registration. Processing logic of the remote computing device may then perform the registration and send registration results back to the first computing device.

The image registration involves determination of the transformations which align one image with the other. Image registration may involve identifying multiple points, point clouds, edges, corners, etc. between the 3D image and the virtual 3D model, surface fitting to the points of the 3D image and the 3D virtual model, and using local searches around points to match points of the image and virtual model. For example, processing logic may match points the image with the closest points interpolated on the surface of the virtual 3D model, and iteratively minimize the distance between matched points. Processing logic may also find the best match of curvature features at points the image with curvature features at points interpolated on the surface of the virtual model, with or without iteration. Other techniques that may be used for image registration include those based on determining point-to-point correspondences using other features and minimization of point-to-surface distances, for example. Other image registration techniques may also be used.

In one embodiment, processing logic may determine a point match between the image and virtual model, which may take the form of a two dimensional (2D) curvature array. A local search for a matching point feature in a corresponding surface patch of another image is carried out by computing features at points sampled in a region surrounding the parametrically similar point. Once corresponding point sets are determined between surface patches of the image and virtual model, determination of the transformation between the two sets of corresponding points in two coordinate frames can be solved. Essentially, an image registration algorithm may compute a transformation between two images that will minimize the distances between points on one surface, and the closest points to them found in the interpolated region on the other image surface can be used as a reference. The transformation may include rotations and/or translational movement in up to six degrees of freedom (e.g., rotations about one to three axes and translations within one to three planes). Additionally, the transformation may include changes in image size (e.g., zooming in or out) for one or both of the images. A result of the image registration may be a transformation matrix that indicates the rotations, translations and/or size changes that will cause the one image to correspond to the other image. In one embodiment, the transformation matrix is applied to the virtual 3D model to cause the 3D image to correlate with the virtual 3D model.

To register the 3D image to the virtual 3D model, processing logic may digitally construct multiple 3D images of the virtual 3D model from different perspectives. Alternatively, if a 2D image is received at block 410, then each of the digitally constructed images may be 2D images. Processing logic may then attempt to register each of the digitally constructed images to the received image until registration is successful for one of the digitally constructed images.

At block 415, processing logic identifies a first set of landmarks (e.g., visible or visual landmarks) and a second set of landmarks (e.g., visible or visual landmarks) on the face from the 3D image. The first set of landmarks may be associated with bony structures such as teeth and the second set of landmarks may be associated with soft facial tissues.

At block 420, processing logic determines a post-treatment arrangement of the first set of visible landmarks based on a first mapping between a current dentition of the person and a post-treatment dentition of the person. The post-treatment dentition may have one or more repositioned and/or reoriented teeth, a different bite pattern, one or more prosthetic teeth, and so on. The first mapping may have been generated based on a treatment plan.

At block 425, processing logic determines, based on applying the post-treatment arrangement of the first set of landmarks to a second mapping between the first set of landmarks and the second set of landmarks, a post-treatment shape of the soft facial tissues. In one embodiment, the first mapping and the second mapping are integrated into a single combined mapping, and the operations of block 420 and block 425 are performed together based on application of the 3D image to the single combined mapping after registration is completed. The first mapping and the second mapping (or a single combined mapping containing the two) may be included in a facial model.

In one embodiment, at block 430 processing logic adjusts the post-treatment shape of the soft facial tissues based on one or more soft facial tissues mechanics functions. The rough positions of the second set of visible landmarks may be determined at block 420 in some embodiments, and those rough positions may be fine-tuned using the soft facial tissue mechanics function or functions.

At block 435, processing logic generates a modified version of the 3D image. Much of features of the modified 3D image may be the same, such as a person's hair, eyes, nose, ears, and so on. Additionally, skin tone, colors, textures, and so forth may be approximately the same between the original 3D image and the modified 3D image. However, the modified 3D image may include the post-treatment dentition of the person as well as changes to the soft facial tissues caused by the post-treatment dentition. For example, if a protruding tooth was causing the lower lip to jut out in the initial image, then the tooth may be repositioned and the lower lip protrusion may be reduced or eliminated in the modified image.

The 3D image may be output to a display. Alternatively, at block 440 a 2D projection of the modified 3D image may be generated at block 440. At block 445, the 2D projection may be output to the display.

At block 450, processing logic may determine if any new 3D (or 2D) images have been received. For example, an image capture device may generate a video of the user's face, and the frames of the video may be processed to find the dental arch and replace it with a corrected dental arch and soft facial tissues, which may be output to display an altered version of the frames of the video that includes the corrected dental arch and soft facial tissues. The smile processing module may continue to generate images of the user's face, and may update the treatment outcome that is shown based on changing lips, changes in the user's smile, movements in the user's head, and so on. If a new image is received, the method returns to block 412 for the new image. If no new image is received, the method ends.

In some embodiments, method 400 may be performed by a computing device of a user at the user's home without the user having to visit a dentist office. For example, the user may download a program that includes smile processing module 108A. The user may input an account identifier (ID) to log into the program. A facial model 182 may have previously been generated for the user. Accordingly, the program may download the facial model 182 from server computing device 130. Method 400 may then be performed by the smile processing module executing on the user's home computing device or mobile computing device.

In some embodiments, processing logic may analyze the relationships and/or angulation between facial features as defined in the modified 3D image. This information can be used to determine that the relationships and/or angulation between facial features is sub-optimal, and to then modify the treatment plan to cause the relationships and/or angulation between facial features to improve. For example, processing logic may analyze the relationship between lip protrusion, jaw protrusion, and angulation of the nose and/or chin. These values may be compared to standard metrics that are considered normal, and may be used to adjust the final dentition in the treatment plan accordingly.

In some embodiments, some operations of method 400 are performed by a first computing device (e.g., a mobile computing device) and other operations are performed by a second computing device with greater processing and/or memory resources (e.g., a server computing device). For example, the operations of at least blocks 410 and 445 may be performed by a first computing device and the operations of one or more of blocks 412-440 may be performed by a second computing device. The first and second computing device may transmit messages (e.g., including images, registration results, etc.) to one another to facilitate the operations.

Figure 5:
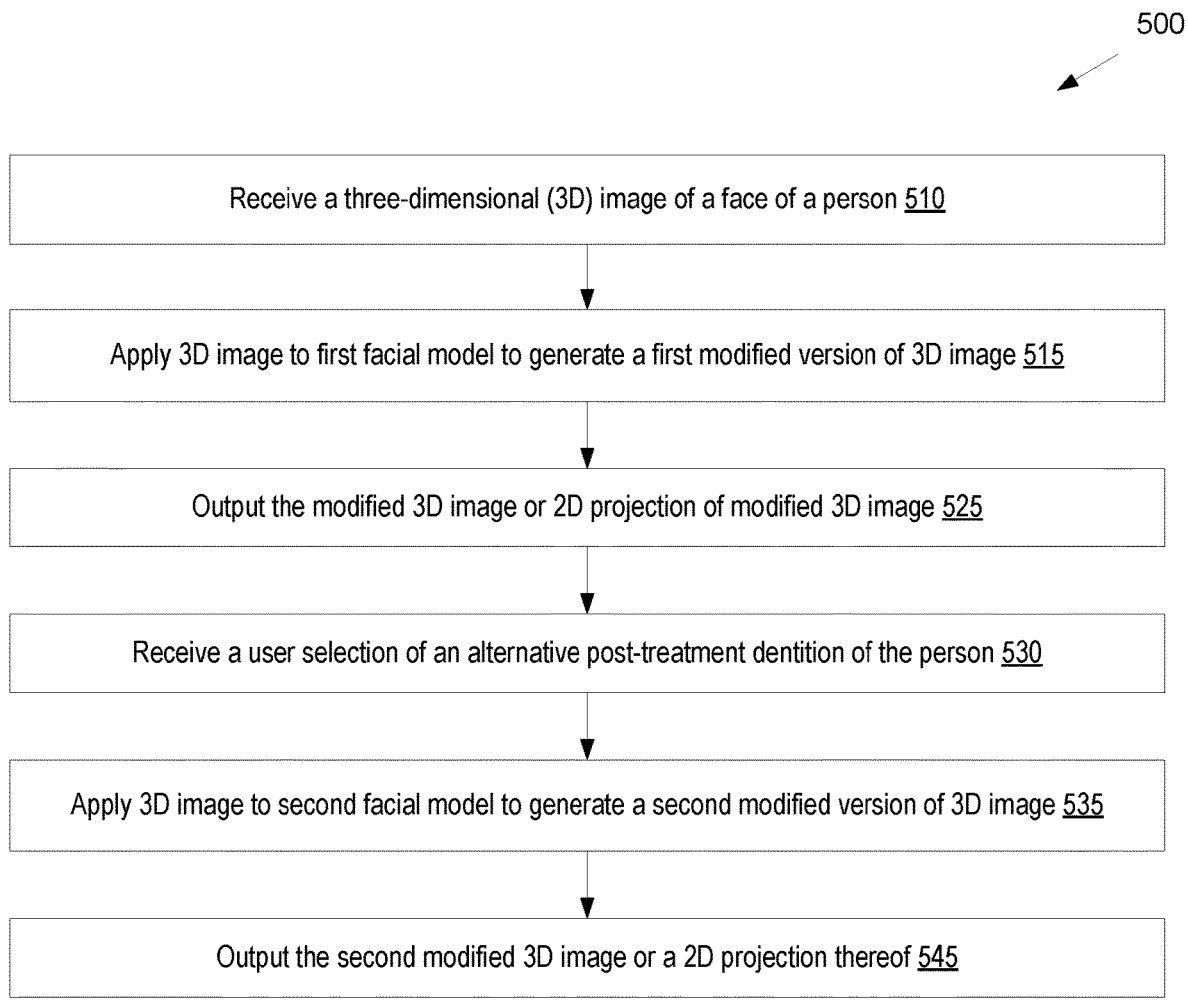
FIG. 5 illustrates a flow diagram for a method of simulating post-treatment images of faces based on pre-treatment images of those faces using a facial model, in accordance with an embodiment.

FIG. 5 illustrates a flow diagram for a method 500 of simulating post-treatment images of faces based on pre-treatment images of those faces using a facial model, in accordance with an embodiment. In some instances a patient may want to select what their final smile will look like. Accordingly, multiple different final treatment outcomes may be generated for the patient, and the patient may be given the option of selecting one of the final treatment outcomes. To enable the user to select a desired final treatment outcome, it may be helpful to show the user what their face and smile will look like for each of the options. Method 500 may be performed in embodiments to give a patient such an experience.

At block 510 of method 500, processing logic receives a 3D image of a face of a person. At block 515, processing logic applies the 3D image to a first facial model to generate a first modified version of the 3D image. The first facial model may have been generated in accordance with methods 200 and/or 300. Applying the 3D image to the first facial model to generate a first modified version of the 3D image may include performing one or more operations of method 400. At block 525, processing logic outputs the modified 3D image or a 2D projection of the modified 3D image.

At block 530, processing logic receives a user selection of an alternative post-treatment dentition of the person (e.g., the user). At block 535, processing logic applies the 3D image to a second facial model to generate a second modified version of the 3D image. The second facial model may have been generated in accordance with methods 200 and/or 300. Applying the 3D image to the second facial model to generate a second modified version of the 3D image may include performing one or more operations of method 400. At block 545, processing logic outputs the second modified 3D image or a 2D projection of the second modified 3D image. The user may then be able to compare their post treatment smiles according to different treatment outcomes in embodiments.

Figure 6:
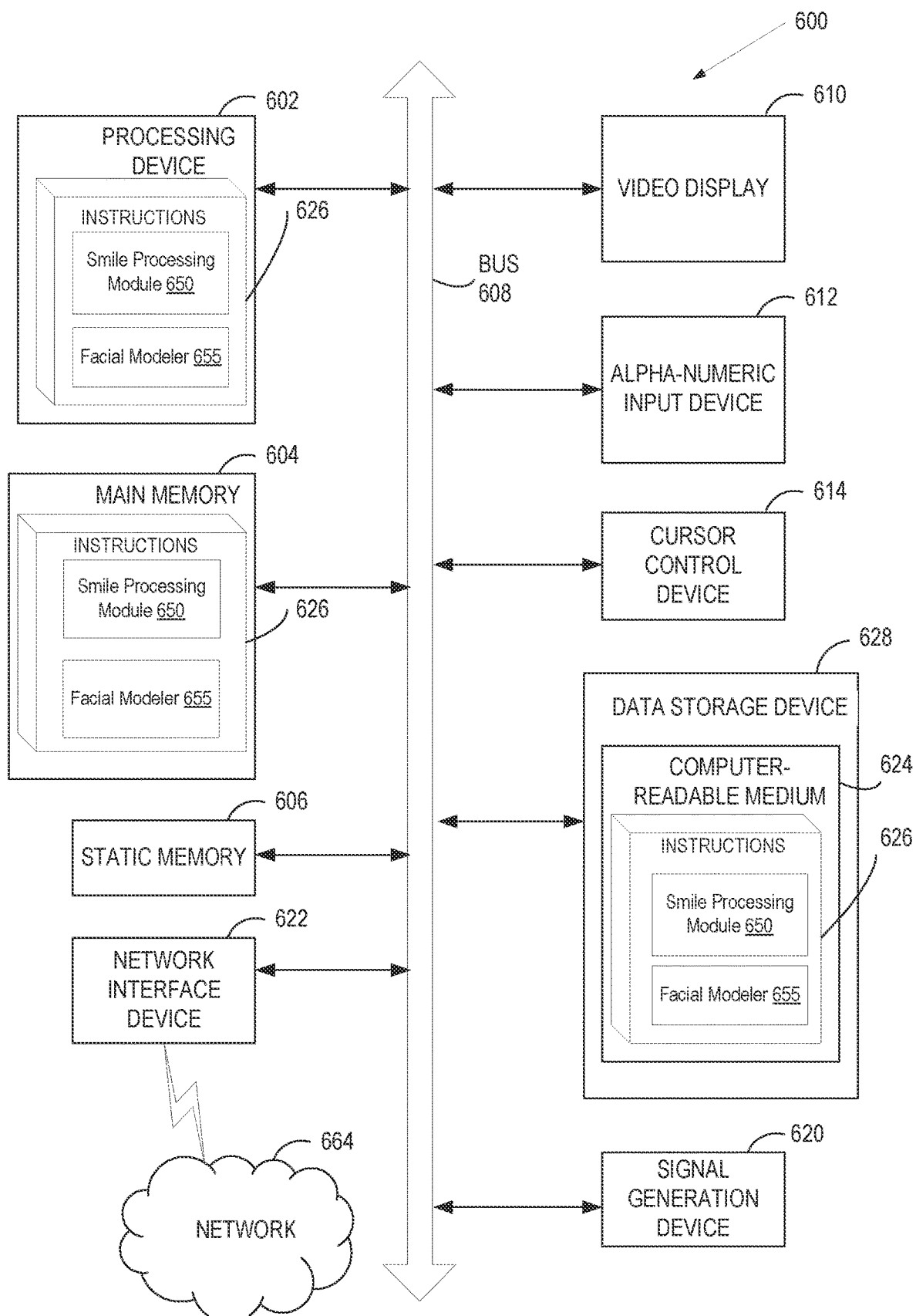
FIG. 6 illustrates a block diagram of an example computing device, in accordance with embodiments of the present disclosure.

FIG. 6 illustrates a diagrammatic representation of a machine in the example form of a computing device 600 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein. In one embodiment, the computer device 600 corresponds to mobile computing device 110 and/or server computing device 130 of FIG. 1.

The example computing device 600 includes a processing device 602, a main memory 604 (e.g., read-only memory (ROM), flash memory, dynamic random access memory (DRAM) such as synchronous DRAM (SDRAM), etc.), a static memory 606 (e.g., flash memory, static random access memory (SRAM), etc.), and a secondary memory (e.g., a data storage device 628), which communicate with each other via a bus 608.

Processing device 602 represents one or more general-purpose processors such as a microprocessor, central processing unit, or the like. More particularly, the processing device 602 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 602 may also be one or more special-purpose processing devices such as an application specific integrated circuit (ASIC), a field programmable gate array (FPGA), a digital signal processor (DSP), network processor, or the like. Processing device 602 is configured to execute the processing logic (instructions 626) for performing operations and steps discussed herein.

The computing device 600 may further include a network interface device 622 for communicating with a network 664. The computing device 600 also may include a video display unit 610 (e.g., a liquid crystal display (LCD) or a cathode ray tube (CRT)), an alphanumeric input device 612 (e.g., a keyboard), a cursor control device 614 (e.g., a mouse), and a signal generation device 620 (e.g., a speaker).

The data storage device 628 may include a machine-readable storage medium (or more specifically a non-transitory computer-readable storage medium) 624 on which is stored one or more sets of instructions 626 embodying any one or more of the methodologies or functions described herein, such as instructions for a smile processing module 650 and/or facial modeler 655. A non-transitory storage medium refers to a storage medium other than a carrier wave. The instructions 626 may also reside, completely or at least partially, within the main memory 604 and/or within the processing device 602 during execution thereof by the computer device 600, the main memory 604 and the processing device 602 also constituting computer-readable storage media.

The computer-readable storage medium 624 may also be used to store a smile processing module 650 and/or facial modeler 655, which may correspond to the similarly named component of FIG. 1. The computer readable storage medium 624 may also store a software library containing methods for a smile processing module 650 and/or facial modeler 655. While the computer-readable storage medium 624 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any non-transitory medium (e.g., computer readable medium other than a carrier wave) that is capable of storing or encoding a set of instructions for execution by the machine and that cause the machine to perform any one or more of the methodologies of the present disclosure. The term "computer-readable medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present disclosure have been described with reference to specific example embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

What is claimed is:

1. A method comprising:
receiving a pre-treatment virtual three-dimensional (3D) model of an upper dental arch and a lower dental arch of a person, the pre-treatment virtual 3D model comprising first positions and orientations of teeth of the upper dental arch and the lower dental arch;

receiving a post-treatment virtual 3D model of the upper dental arch and the lower dental arch of the person, the post-treatment virtual 3D model comprising second positions and orientations of the teeth of the upper dental arch and the lower dental arch, wherein for at least one tooth the second positions and orientations are different from the first positions and orientations;

determining a first mapping between first positions of a first plurality of landmarks associated with the teeth in the pre-treatment virtual 3D model and second positions of the first plurality of landmarks associated with the teeth in the post-treatment virtual 3D model;

receiving an image of a face of the person, wherein the image comprises at least a portion of the teeth and soft facial tissues;

generating a second mapping between the first plurality of landmarks associated with the teeth and a second plurality of landmarks associated with the soft facial tissues from the image of the face of the person; and generating a facial model comprising the first mapping and the second mapping, wherein the facial model generates post-treatment images of the teeth and the soft facial tissues based on pre-treatment images of the teeth and the soft facial tissues.

2. The method of claim 1, wherein the image comprises a cone beam computed tomography (CBCT) image of the face of the person.

3. The method of claim 1, further comprising:
outputting instructions for the person to perform a plurality of facial expressions;
receiving a plurality of 3D images of the face of the person, wherein each 3D image of the plurality of 3D images is associated with one of the plurality of facial expressions;
making a determination of how the soft facial tissues respond to the plurality of facial expressions from the plurality of 3D images; and
refining the facial model based on the determination of how the soft facial tissues respond to the plurality of facial expressions.

4. The method of claim 1, further comprising:
receiving a new three-dimensional (3D) image of the face of the person; and
generating a post treatment image of the face of the person based on applying the new 3D image to the facial model, wherein generating the post treatment image comprises:
identifying the first plurality of landmarks and the second plurality of landmarks on the face from the new 3D image;
determining a post-treatment arrangement of the first plurality of landmarks based on the first mapping;
determining, based on applying the post-treatment arrangement of the first plurality of landmarks to the second mapping between the first plurality of landmarks and the second plurality of landmarks, a post-treatment shape of the soft facial tissues; and
generating a modified version of the new 3D image, wherein the soft facial tissues have the post-treatment shape in the modified version of the new 3D image.

5. The method of claim 4, further comprising:
generating a two-dimensional (2D) projection of the modified version of the new 3D image; and
outputting the 2D projection to a display.

6. The method of claim 4, further comprising:
registering the new 3D image of the face to the pre-treatment virtual 3D model.

7. The method of claim 1, further comprising:
receiving a second post-treatment virtual 3D model of the upper dental arch and the lower dental arch of the person, the second post-treatment virtual 3D model comprising third positions and orientations of the teeth of the upper dental arch and the lower dental arch, wherein for at least one tooth the third positions and orientations are different from the first positions and orientations;
determining a third mapping between the first positions of the first plurality of landmarks associated with the teeth in the pre-treatment virtual 3D model and third positions of the first plurality of landmarks associated with the teeth in the second post-treatment virtual 3D model; and
generating a second facial model comprising the third mapping and the second mapping, wherein the second facial model generates different post-treatment images of the teeth and the soft facial tissues based on the pre-treatment images of the teeth and the soft facial tissues.

8. The method of claim 7, further comprising:
receiving a new three-dimensional (3D) image of the face of the person; and
generating a first post treatment image of the face of the person based on applying the new 3D image to the facial model;
receiving a user selection of the second facial model; and
generating a second post treatment image of the face of the person based on applying the new 3D image to the second facial model.

9. A non-transitory computer readable medium comprising instructions that, when executed by a processing device, cause the processing device to perform operations comprising:
receiving a pre-treatment virtual three-dimensional (3D) model of an upper dental arch and a lower dental arch of a person, the pre-treatment virtual 3D model comprising first positions and orientations of teeth of the upper dental arch and the lower dental arch;
receiving a post-treatment virtual 3D model of the upper dental arch and the lower dental arch of the person, the post-treatment virtual 3D model comprising second positions and orientations of the teeth of the upper dental arch and the lower dental arch, wherein for at least one tooth the second positions and orientations are different from the first positions and orientations;
determining a first mapping between first positions of a first plurality of landmarks associated with the teeth in the pre-treatment virtual 3D model and second positions of the first plurality of landmarks associated with the teeth in the post-treatment virtual 3D model;
receiving an image of a face of the person, wherein the image comprises at least a portion of the teeth and soft facial tissues;
generating a second mapping between the first plurality of landmarks associated with the teeth and a second plurality of landmarks associated with the soft facial tissues from the image of the face of the person; and
generating a facial model comprising the first mapping and the second mapping, wherein the facial model generates post-treatment images of the teeth and the soft facial tissues based on pre-treatment images of the teeth and the soft facial tissues.

10. The non-transitory computer readable medium of claim 9, wherein the image comprises a cone beam computed tomography (CBCT) image of the face of the person.

11. The non-transitory computer readable medium of claim 9, the operations further comprising:
outputting instructions for the person to perform a plurality of facial expressions;
receiving a plurality of 3D images of the face of the person, wherein each 3D image of the plurality of 3D images is associated with one of the plurality of facial expressions;
making a determination of how the soft facial tissues respond to the plurality of facial expressions from the plurality of 3D images; and
refining the facial model based on the determination of how the soft facial tissues respond to the plurality of facial expressions.

12. The non-transitory computer readable medium of claim 9, the operations further comprising:
receiving a new three-dimensional (3D) image of the face of the person; and
generating a post treatment image of the face of the person based on applying the new 3D image to the facial model, wherein generating the post treatment image comprises:
identifying the first plurality of landmarks and the second plurality of landmarks on the face from the new 3D image;
determining a post-treatment arrangement of the first plurality of landmarks based on the first mapping;
determining, based on applying the post-treatment arrangement of the first plurality of landmarks to the second mapping between the first plurality of landmarks and the second plurality of landmarks, a post-treatment shape of the soft facial tissues; and
generating a modified version of the new 3D image, wherein the soft facial tissues have the post-treatment shape in the modified version of the new 3D image.

13. The non-transitory computer readable medium of claim 12, the operations further comprising:
generating a two-dimensional (2D) projection of the modified version of the new 3D image; and
outputting the 2D projection to a display.

14. The non-transitory computer readable medium of claim 12, the operations further comprising:
registering the new 3D image of the face to the pre-treatment virtual 3D model.

15. The non-transitory computer readable medium of claim 9, the operations further comprising:
receiving a second post-treatment virtual 3D model of the upper dental arch and the lower dental arch of the person, the second post-treatment virtual 3D model comprising third positions and orientations of the teeth of the upper dental arch and the lower dental arch, wherein for at least one tooth the third positions and orientations are different from the first positions and orientations;
determining a third mapping between the first positions of the first plurality of landmarks associated with the teeth in the pre-treatment virtual 3D model and third positions of the first plurality of landmarks associated with the teeth in the second post-treatment virtual 3D model; and
generating a second facial model comprising the third mapping and the second mapping, wherein the second facial model generates different post-treatment images of the teeth and the soft facial tissues based on the pre-treatment images of the teeth and the soft facial tissues.

16. The non-transitory computer readable medium of claim 15, the operations further comprising:
receiving a new three-dimensional (3D) image of the face of the person; and
generating a first post treatment image of the face of the person based on applying the new 3D image to the facial model;
receiving a user selection of the second facial model; and
generating a second post treatment image of the face of the person based on applying the new 3D image to the second facial model.

17. A system comprising:
a memory; and
a processing device operatively coupled to the memory, the processing device to:
receive a pre-treatment virtual three-dimensional (3D) model of an upper dental arch and a lower dental arch of a person, the pre-treatment virtual 3D model comprising first positions and orientations of teeth of the upper dental arch and the lower dental arch;
receive a post-treatment virtual 3D model of the upper dental arch and the lower dental arch of the person, the post-treatment virtual 3D model comprising second positions and orientations of the teeth of the upper dental arch and the lower dental arch, wherein for at least one tooth the second positions and orientations are different from the first positions and orientations;
determine a first mapping between first positions of a first plurality of landmarks associated with the teeth in the pre-treatment virtual 3D model and second positions of the first plurality of landmarks associated with the teeth in the post-treatment virtual 3D model;
receive an image of a face of the person, wherein the image comprises at least a portion of the teeth and soft facial tissues;
generate a second mapping between the first plurality of landmarks associated with the teeth and a second plurality of landmarks associated with the soft facial tissues from the image of the face of the person; and
generate a facial model comprising the first mapping and the second mapping, wherein the facial model generates post-treatment images of the teeth and the soft facial tissues based on pre-treatment images of the teeth and the soft facial tissues.

18. The system of claim 17, wherein the image comprises a cone beam computed tomography (CBCT) image of the face of the person.

19. The system of claim 17, wherein the processing device is further to:
output instructions for the person to perform a plurality of facial expressions;
receive a plurality of 3D images of the face of the person, wherein each 3D image of the plurality of 3D images is associated with one of the plurality of facial expressions;
make a determination of how the soft facial tissues respond to the plurality of facial expressions from the plurality of 3D images; and
refine the facial model based on the determination of how the soft facial tissues respond to the plurality of facial expressions.

20. The system of claim 17, wherein the processing device is further to:
receive a new three-dimensional (3D) image of the face of the person; and
generate a post treatment image of the face of the person based on applying the new 3D image to the facial model, wherein generating the post treatment image comprises:
identify the first plurality of landmarks and the second plurality of landmarks on the face from the new 3D image;
determine a post-treatment arrangement of the first plurality of landmarks based on the first mapping;
determine, based on applying the post-treatment arrangement of the first plurality of landmarks to the second mapping between the first plurality of landmarks and the second plurality of landmarks, a post-treatment shape of the soft facial tissues; and
generate a modified version of the new 3D image, wherein the soft facial tissues have the post-treatment shape in the modified version of the new 3D image.

21. The system of claim 20, wherein the processing device is further to:
generate a two-dimensional (2D) projection of the modified version of the new 3D image; and
output the 2D projection to a display.

22. The system of claim 20, wherein the processing device is further to:
register the new 3D image of the face to the pre-treatment virtual 3D model.

23. The system of claim 17, wherein the processing device is further to:
receive a second post-treatment virtual 3D model of the upper dental arch and the lower dental arch of the person, the second post-treatment virtual 3D model comprising third positions and orientations of the teeth of the upper dental arch and the lower dental arch, wherein for at least one tooth the third positions and orientations are different from the first positions and orientations;
determine a third mapping between the first positions of the first plurality of landmarks associated with the teeth in the pre-treatment virtual 3D model and third positions of the first plurality of landmarks associated with the teeth in the second post-treatment virtual 3D model; and
generate a second facial model comprising the third mapping and the second mapping, wherein the second facial model generates different post-treatment images of the teeth and the soft facial tissues based on the pre-treatment images of the teeth and the soft facial tissues.

24. The system of claim 23, wherein the system is further to:
receive a new three-dimensional (3D) image of the face of the person; and
generate a first post treatment image of the face of the person based on applying the new 3D image to the facial model;
receive a user selection of the second facial model; and
generate a second post treatment image of the face of the person based on applying the new 3D image to the second facial model.

* * * * *